United States Patent
Suzuki et al.

(10) Patent No.: US 10,561,141 B2
(45) Date of Patent: Feb. 18, 2020

(54) COLLECTED BIOLOGICAL TISSUE CRYOPRESERVATION TOOL AND METHOD FOR FREEZING COLLECTED TISSUE FRAGMENT

(71) Applicants: Kitazato BioPharma Co., Ltd., Fuji-shi, Shizuoka (JP); St. Marianna University School of Medicine, Kawasaki-shi, Kanagawa (JP)

(72) Inventors: Nao Suzuki, Tokyo (JP); Yodo Sugishita, Yokohama (JP); Futoshi Inoue, Fujinomiya (JP)

(73) Assignees: KITAZATO CORPORATION, Fuji-Shi, Shizuoka (JP); ST. MARIANNA UNIVERSITY SCHOOL OF MEDICINE, Kawasaki-Shi, Kanagawa (JP)

( * ) Notice: Subject to any disclaimer, the term of this patent is extended or adjusted under 35 U.S.C. 154(b) by 136 days.

(21) Appl. No.: 15/611,276

(22) Filed: Jun. 1, 2017

(65) Prior Publication Data
US 2017/0265457 A1    Sep. 21, 2017

Related U.S. Application Data (63) Continuation of application No. PCT/JP2015/083634, filed on Nov. 30, 2015.

(30) Foreign Application Priority Data

Dec. 2, 2014    (JP) .................. 2014-244413

(51) Int. Cl.
*A01N 1/00*    (2006.01)
*A01N 1/02*    (2006.01)
*C12M 1/00*    (2006.01)

(52) U.S. Cl.
CPC ............. *A01N 1/0268* (2013.01); *A01N 1/02* (2013.01); *A01N 1/021* (2013.01); *C12M 1/00* (2013.01)

(58) Field of Classification Search
CPC .................... A01N 1/0268; A01N 1/02
See application file for complete search history.

(56) References Cited

U.S. PATENT DOCUMENTS

| | | |
|---|---|---|
| 4,797,261 A | 1/1989 | Swann et al. |
| 5,964,096 A | 10/1999 | Watson et al. |

(Continued)

FOREIGN PATENT DOCUMENTS

| | | |
|---|---|---|
| DE | 102 62 157 B4 | 11/2006 |
| JP | 2000-189155 A | 7/2000 |

(Continued)

OTHER PUBLICATIONS

International Search Report (PCT/ISA/210) dated Mar. 1, 2016, by the Japanese Patent Office as the International Searching Authority for International Application No. PCT/JP2015/083634.

(Continued)

*Primary Examiner* — Kara D Johnson
(74) *Attorney, Agent, or Firm* — Buchanan Ingersoll & Rooney PC (57) ABSTRACT

A collected living tissue cryopreserving tool is composed of a tissue piece holder and a resin-made accommodating bag. The tissue piece holder is composed of a plate-shaped body part including a thermally conductive plate-shaped lower member and a plate-shaped upper member and a covering sheet held by the plate-shaped body part. The tissue piece holder has a tissue piece placing part formed of a cut-out part provided on the plate-shaped upper member and a part, of an upper surface of the thermally conductive plate-shaped lower member, which is disposed at the cut-out part. The (Continued)

covering sheet is capable of covering the tissue piece placing part.

12 Claims, 8 Drawing Sheets

(56) References Cited

U.S. PATENT DOCUMENTS

| | | |
|---|---|---|
| 2008/0050284 A1 | 2/2008 | Lorsch |
| 2009/0065507 A1 | 3/2009 | Ishihara et al. |
| 2013/0137080 A1 | 5/2013 | Henderson et al. |
| 2014/0234956 A1* | 8/2014 | Inoue .................. A01N 1/0268 435/307.1 |
| 2015/0044765 A1 | 2/2015 | Inoue |
| 2016/0057991 A1* | 3/2016 | Matsuzawa .......... A01N 1/0231 435/374 |

FOREIGN PATENT DOCUMENTS

| | | | |
|---|---|---|---|
| JP | 2002315573 A * | 10/2002 | ............... A01N 1/02 |
| JP | 2003-284546 A | 10/2003 | |
| JP | 2008-222640 A | 9/2008 | |
| JP | 2012-219017 A | 11/2012 | |
| WO | WO 2006/101238 A1 | 9/2006 | |
| WO | WO 2013/051521 A1 | 4/2013 | |

OTHER PUBLICATIONS

Written Opinion (PCT/ISA/237) dated Mar. 1, 2016, by the Japanese Patent Office as the International Searching Authority for International Application No. PCT/JP2015/083634.

The extended European Search Report dated Aug. 3, 2018, by the European Patent Office in corresponding European Patent Application No. 15864995.4-1124. (6 pages).

* cited by examiner

COLLECTED BIOLOGICAL TISSUE CRYOPRESERVATION TOOL AND METHOD FOR FREEZING COLLECTED TISSUE FRAGMENT

TECHNICAL FIELD

The present invention relates to a collected living tissue cryopreserving tool and a collected tissue piece freezing method to be used in cryopreserving living cells such as mammalian ova.

BACKGROUND ART

Living cells (for example, sperm, ovum, and the like) of mammals are cryopreserved. The cryopreservation of the living cells enables the preservation of hereditary resources of a specified system and kind and is effective for maintaining animal species standing on the verge of extinction and useful for human infertility treatment.

A method of freezing the ovary is disclosed in Japanese Patent Application Laid-Open Publication No. 2003-284546 (patent document 1). The ovary freezing method is characterized in that a reproductive tissue including at least the ovary taken out from a female individual of an impersonal mammal is preserved at 15 to zero degrees C. and thereafter frozen by a vitrification method.

As a method for freezing mammalian embryos, as disclosed in a patent document 1 (Japanese Patent Application Laid-Open Publication 2000-189155), there is proposed a method for freezing and storing mammalian embryos that mammalian embryos or ova are bonded to the inner surface of the freezing and storing container such as the sterilized frozen straw, frozen vial or frozen tube by using a vitrified liquid in an amount minimum and enough to enclose the mammalian embryos or the ova therewith. The freezing and storing container is sealed and rapidly cooled by bringing the freezing and storing container into contact with liquid nitrogen. In the thawing method, the freezing and storing container stored in the above method is taken out of the liquid nitrogen and one end thereof is opened. A diluted liquid of 33 to 39 degree C. is injected directly into the container to thaw the mammalian embryos or the ova and dilute the vitrified liquid. This method eliminates a possibility that the mammalian embryos or the ova are infected with a disease through viruses or bacteria and is capable of storing them at a high survival rate and thawing them and diluting the vitrified liquid.

The present applicant proposed the tissue piece cryopreserving plate as disclosed in Japanese Patent Application Laid-Open Publication No. 2008-222640 (patent document 3). The tissue piece cryopreserving plate is the plate-shaped metal member which has the width equal to or a little larger than the predetermined width of the cutting portion-specifying open portion, is extendable at a predetermined length, allows the tissue piece cut off from a living tissue bye using the tissue cutting position-specifying tool to be placed thereon, and has a large number of holes.

The present applicant proposed the cryopreserving tool as disclosed in Japanese Patent Application Laid-Open Publication No. 2012-219017 (patent document 4). The cryopreserving tool of the patent document 4 is used to freeze a biospecimen such as a tissue piece, a cell, and the like by means of a vitrification freezing method (rapid vitrification freezing method and super-rapid vitrification freezing method). The cryopreserving tool has the specimen placing part including the stainless sheet and the holding part fixed to the proximal end portion of the specimen placing part. The cryopreserving tool does not have a through-hole in the region of the specimen placing part where the biospecimen is to be placed, but the stainless sheet is used as the specimen placing part.

PRIOR ART DOCUMENTS

Patent Documents

Patent document 1: Japanese Patent Application Laid-Open Publication No. 2003-284546
Patent document 2: Japanese Patent Application Laid-Open Publication No. 2000-189155
Patent document 3: Japanese Patent Application Laid-Open Publication No. 2008-222640
Patent document 4: Japanese Patent Application Laid-Open Publication No. 2012-219017

SUMMARY OF THE INVENTION

Problem to be Solved by the Invention

The tissue piece cryopreserving plate and the cryopreserving tool disclosed in the patent documents 3 and 4 respectively are effective for freezing the tissue piece by vitrification. Both of the tissue piece cryopreserving plate and the cryopreserving tool are based on the premise that the collected tissue piece is directly brought into contact with the liquid nitrogen which is the cooling medium and that the container accommodating the collected tissue piece is directly brought into contact with the cooling medium (liquid nitrogen) during cryopreservation of the tissue piece. But a long-term contact between the container and the cooling medium (liquid nitrogen) may cause the container to deteriorate and the cooling medium to flow thereinto. The direct contact of the collected tissue piece with the cooling medium is effective for freezing the tissue piece by vitrification. But if possible, the direct contact of such a substance with cells should be avoided.

In the tissue piece cryopreserving plate and the cryopreserving tool disclosed in the patent documents 3 and 4 respectively, the container accommodating the living tissue and the tissue piece placing part are sealed with the liquid nitrogen attaching thereto. After the living tissue is cryopreserved, the container is opened in a normal temperature environment when the living tissue is used. When the container is opened without gradually performing an opening operation, owing to an inner pressure caused by the liquid nitrogen vaporized inside the container, there is a possibility that the living tissue piece placed on the tissue piece placing part may be scattered. Thus, it is necessary to carefully perform the opening operation.

It is an object of the present invention to provide a collected living tissue cryopreserving tool and a collected tissue piece freezing method which allow a freezing operation to be performed without bringing a collected living tissue piece into contact with a cooling medium and allow the collected living tissue piece to be rapidly frozen, prevents the living tissue piece from contacting the cooling medium when it is cryopreserved for a long time, and prevents the living tissue piece from scattering when an operation of taking out the cryopreserved living tissue piece from an accommodating bag is performed.

Means for Solving the Problems

The means for achieving the above-described object is as described below.

A collected living tissue cryopreserving tool for cryopreserving a collected living tissue piece in a sealed state, said collected living tissue cryopreserving tool comprising a tissue piece holder capable of holding said living tissue piece and a resin-made accommodating bag which is capable of accommodating said tissue piece holder therein, sealable by being heat-sealed after accommodating said tissue piece holder therein, and resistant to liquid nitrogen, wherein said tissue piece holder comprises a plate-shaped body part composed of a thermally conductive plate-shaped lower member and a plate-shaped upper member fixed to an upper surface of said thermally conductive plate-shaped lower member and a covering sheet held by said plate-shaped body part; said tissue piece holder has a tissue piece placing part formed of a cut-out part provided on said plate-shaped upper member and a part, of said upper surface of said thermally conductive plate-shaped lower member, which is disposed at said cut-out part; and said covering sheet is capable of entirely covering said tissue piece placing part and a peripheral portion of said tissue piece placing part.

The means for achieving the above-described object is as described below.

A collected living tissue cryopreserving tool for cryopreserving a collected living tissue piece in a sealed state, said collected living tissue cryopreserving tool comprising a tissue piece holder capable of holding said living tissue piece and a resin-made accommodating bag which is capable of accommodating said tissue piece holder therein, sealable by being heat-sealed after accommodating said tissue piece holder therein, and resistant to liquid nitrogen, wherein said tissue piece holder comprises a thermally conductive plate-shaped body part and a covering sheet held by said plate-shaped body part; said tissue piece holder has a tissue piece placing part formed on said, plate-shaped body part; and said covering sheet is capable of entirely covering said tissue piece placing part and a peripheral portion of said tissue piece placing part.

The means for achieving the above-described object as described below.

A collected tissue piece freezing method to be carried out by using any one of collected living tissue cryopreserving tool, said collected tissue piece freezing method comprising a tissue piece immersing step of immersing a collected tissue piece in a vitrification solution; a tissue piece placing step of placing said tissue piece taken out from said vitrification solution on said tissue piece placing part of said tissue piece holder; a tissue piece covering step of covering said tissue piece placed on said tissue piece placing part with said covering sheet and bringing said covering sheet into close contact with said tissue piece; an accommodating and sealing step of accommodating said tissue piece holder holding said tissue piece inside said accommodating bag without bringing said tissue piece holder into contact with a cooling medium and heat-sealing an open portion of said accommodating bag; and a freezing step of freezing said tissue piece by accommodating said tissue piece holder inside said accommodating bag and bringing said sealed collected living tissue cryopreserving tool into contact with said cooling medium.

MODE FOR CARRYING OUT THE INVENTION

The collected living tissue cryopreserving tool of the present invention and the tissue piece freezing method thereof are described below by using the embodiments shown in the drawings.

A collected living tissue cryopreserving tool 10 of the present invention is used to cryopreserve a collected living tissue piece in a sealed state. The collected living tissue cryopreserving tool 10 is composed of a tissue piece holder 1 capable of holding the living tissue piece and a resin-made accommodating bag 11 which is capable of accommodating the tissue piece holder 1 therein, sealable by being heat-sealed after accommodating the tissue piece holder therein, and resistant to liquid nitrogen. The tissue piece holder 1 is composed of a thermally conductive plate-shaped body part and a covering sheet 4 held by the plate-shaped body part. The tissue piece holder 1 has a tissue piece placing part 5 provided on the plate-shaped body part. The covering sheet 4 is capable of entirely covering the tissue piece placing part 5 and a peripheral portion of the tissue piece placing part.

The collected living tissue cryopreserving tool 10 of the present invention is composed of the tissue piece holder 1 capable of holding the living tissue and the resin-made accommodating bag 11 which is capable of accommodating the tissue piece holder 1 therein, sealable by being heat-sealed after accommodating the tissue piece holder, and resistant to liquid nitrogen. The tissue piece holder 1 is composed of the plate-shaped body part including a thermally conductive plate-shaped lower member 2 and a plate-shaped upper member 3 fixed to an upper surface of the thermally conductive plate-shaped lower member 2 and the covering sheet 4 held by the plate-shaped body part. The tissue piece holder 1 has the tissue piece placing part 5 formed of a cut-out part 32 provided on the plate-shaped upper member 3 and a part, of the upper surface of the thermally conductive plate-shaped lower member 2, which is disposed at the cut-out part 32. The covering sheet 4 is capable of entirely covering the tissue piece placing part 5 and the peripheral portion of the tissue piece placing part 5.

Figure 1:
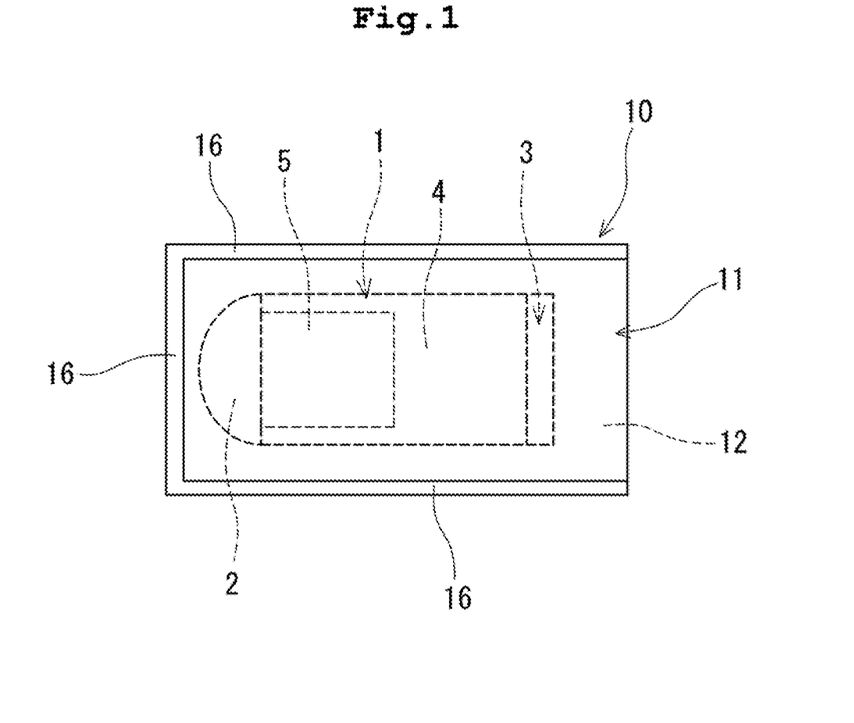
FIG. 1 is a front view of one embodiment of a collected living tissue cryopreserving tool of the present invention.

As shown in FIG. 1, the collected living tissue cryopreserving tool 1 is composed of the tissue piece holder 1 and the resin-made accommodating bag 11 for accommodating the tissue piece holder 1 therein.

As shown in FIGS. 2 through 10, the tissue piece holder 1 is composed of the plate-shaped body part and the covering sheet 4 held by the plate-shaped body part.

The plate-shaped body part is composed of the thermally conductive plate-shaped lower member 2 and the plate-shaped upper member 3 fixed to the upper surface of the thermally conductive plate-shaped lower member 2.

As shown in FIGS. 2 through 10 (best shown in FIG. 7), the thermally conductive plate-shaped lower member 2 is made of a metal plate approximately rectangular. The thermally conductive plate-shaped lower member of this embodiment has a one end portion 21 rounded at both corners thereof and an approximately rectangular part 20 extended from the one end portion 21 thereof to the other end portion thereof. The one end portion 21 of the thermally conductive plate-shaped lower member 2 of this embodiment is approximately semicircular. Because the thermally conductive plate-shaped lower member has the one end portion having the above-described configuration, the tissue piece holder 1 can be easily inserted into the accommodating bag 11.

As the thermally conductive plate-shaped lower member 2, it is preferable to use a metallic plate-shaped member, a graphite sheet, and the like having a high thermal conductivity. As metals forming the metallic plate-shaped member, metals selected from among copper, copper alloys, aluminum, aluminum alloys, gold, gold alloys, silver, silver alloys, stainless steel alloys, titanium, and titanium alloys are preferable. The thickness of the thermally conductive plate-shaped lower member 2 is set to favorably 0.1 to 3 mm and especially favorably 0.5 to 2 mm. The width of the thermally conductive plate-shaped lower member 2 is set to favorably 8 to 25 mm and especially favorably 10 to 20 mm. The whole length of the thermally conductive plate-shaped lower member 2 is set to favorably 30 to 50 mm and especially favorably 35 to 45 mm. The length of the rectangular part of the thermally conductive plate-shaped lower member is set to favorably 25 to 35 mm. The length of the one end portion of the thermally conductive plate-shaped lower member rounded at both corners thereof is set to favorably 5 to 15 mm.

As shown in FIGS. 2 through 10 (particularly, in FIG. 7), the plate-shaped upper member 3 is disposed on the upper surface of the thermally conductive plate-shaped lower member 2. More specifically, the plate-shaped upper member 3 is placed on an upper surface of the rectangular part 20 of the thermally conductive plate-shaped lower member 2 and fixed thereto. The configuration of the plate-shaped upper member 3 is almost the same as that of the rectangular part 21 of the thermally conductive plate-shaped lower member 2.

Figure 7:
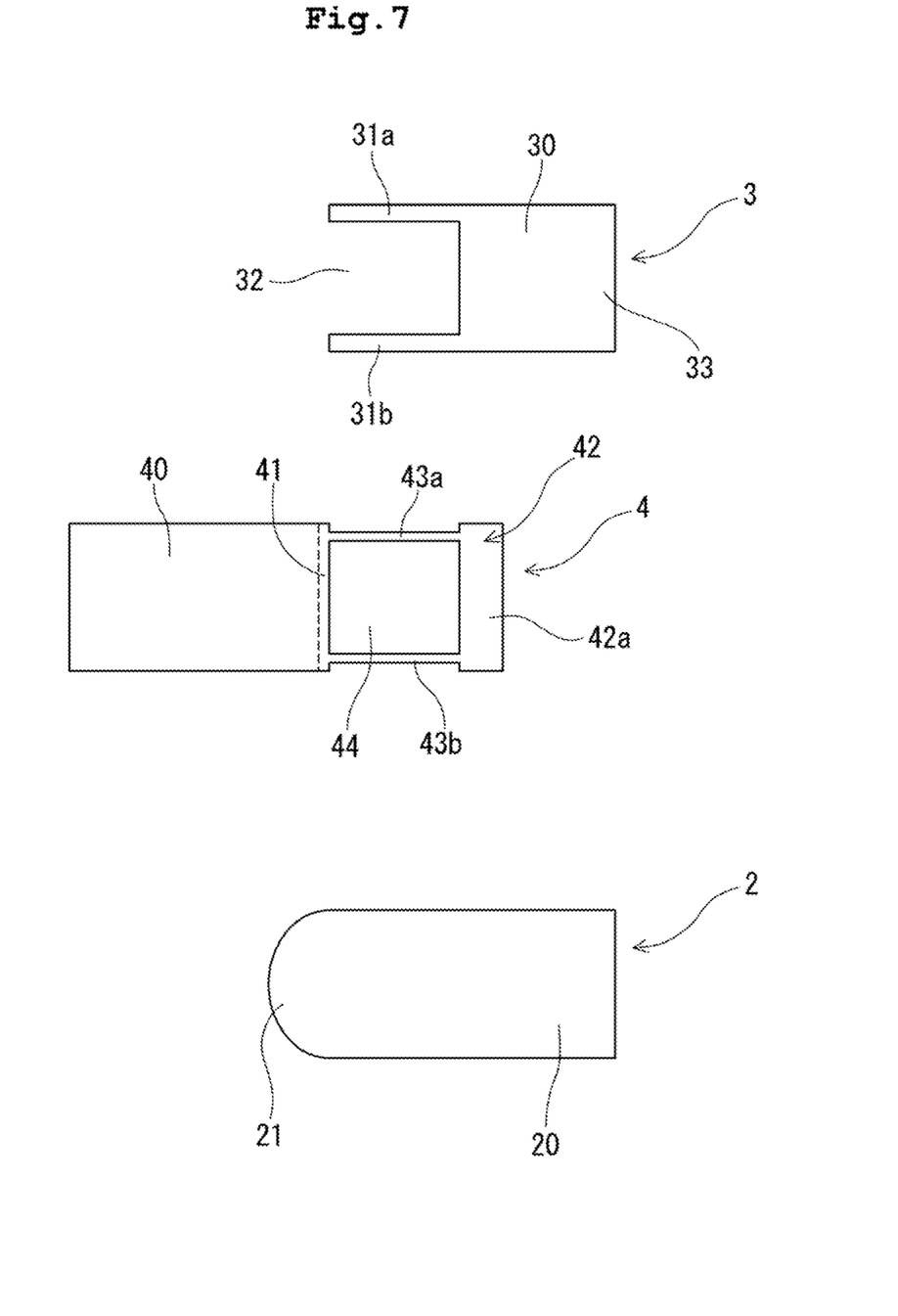
FIG. 7 is an explanatory view for explaining constituent members of the tissue piece holder shown in FIG. 2.

The plate-shaped upper member 3 has the cut-out part 32 extended from its one end side toward its other end side. The plate-shaped upper member 3 of this embodiment is so disposed that one end thereof having the cut-out part 32 is positioned in the vicinity of one end of the approximately rectangular part of the thermally conductive plate-shaped lower member 2. In this embodiment, the cut-out part 32 is extended at a predetermined length from the one end (in the vicinity of one end of rectangular part 20 of thermally conductive plate-shaped lower member 2) of the plate-shaped upper member 3 toward its other end side. Therefore, as shown in FIG. 7, the plate-shaped upper member 3 has two extended portions 31*a*, 31*b* projected from one end of a flat plate part 30.

The cut-out part 32 is open at its one end, whereas other edges of the cut-out part is surrounded with the two extended portions 31*a*, 31*b* and the flat plate part 30. The size of the cut-out part 32 is set to favorably 30 to 250 mm$^2$, more favorably 40 to 230 mm$^2$, and most favorably 50 to 200 mm$^2$. The width of the cut-out part 32 is set to favorably 6 to 20 mm and especially favorably 8 to 17 mm. Although the cut-out part 32 is rectangular in this embodiment, the configuration thereof is not limited to the rectangular configuration. The cut-out part may be circular, semicircular, polygonal or semi-polygonal. The whole length of the plate-shaped upper member 3 is set to favorably 15 to 45 mm and especially favorably 20 to 40 mm. It is preferable to set the width of the plate-shaped upper member 3 equally to or a little smaller than that of the thermally conductive plate-shaped lower member 2. More specifically, the width of the plate-shaped upper member 3 is set to favorably 8 to 25 mm and especially favorably 10 to 20 mm.

Although it is preferable to use a metallic plate-shaped member, a graphite sheet, and the like having a high thermal conductivity as the plate-shaped upper member 3, a synthetic resin-made plate may be used. As metals forming the metallic plate-shaped member, metals selected from among copper, copper alloys, aluminum, aluminum alloys, gold, gold alloys, silver, silver alloys, stainless steel alloys, titanium, and titanium alloys are preferable.

The tissue piece holder 1 has the tissue piece placing part 5 formed of the cut-out part 32 provided on the plate-shaped upper member 3 and a part, of the upper surface of the thermally conductive plate-shaped lower member 2, which is disposed at the cut-out part 32. The size of the tissue piece placing part 5 is set to favorably 30 to 250 mm$^2$, more favorably 40 to 230 mm$^2$, and most favorably 50 to 200 mm$^2$. A tissue piece having a size of 5×5 mm to 10×10 mm is placed on the tissue piece placing part 5.

As shown in FIGS. 2 through 10 (particularly, FIG. 7), the covering sheet 4 is capable of entirely covering the tissue piece placing part 5 and the peripheral portion of the tissue piece placing part 5. In this embodiment, one end side part of the covering sheet 4 is formed as a coverable part 40 capable of covering the tissue piece placing part. The other end side part 42 of the covering sheet is sandwiched between the thermally conductive plate-shaped lower member 2 and the plate-shaped upper member 3. The covering sheet 4 is foldable at one end of the plate-shaped upper member 3.

Figure 2:
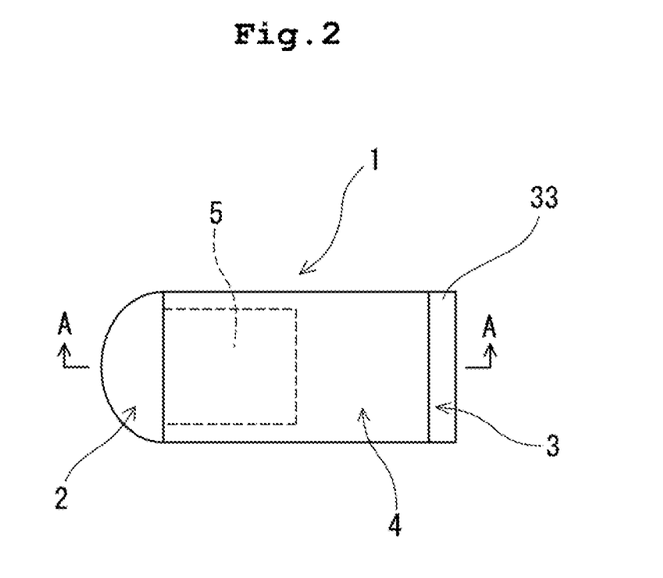
FIG. 2 is a front view of a tissue piece holder for use in the collected living tissue cryopreserving tool shown in FIG. 1.

By folding back the covering sheet 4, the covering sheet 4 is capable of entirely covering the tissue piece placing part 5 and the peripheral portion, of the tissue piece placing part 5. The covering sheet 4 of this embodiment is extended beyond the tissue piece placing part 5 and capable of covering a part of an upper surface of the plate-shaped upper member between one end of the plate-shaped upper member and the tissue piece placing part 5 or almost an entirety of the upper surfaces of the plate-shaped upper member between one end of the plate-shaped upper member and the tissue piece placing part 5. In the tissue piece holder 1 of this embodiment, as shown in FIG. 2, when the plate-shaped upper member 3 is covered with the covering sheet 4, the other end portion 33 of the plate-shaped upper member 3 is exposed to the outside.

It is preferable that the covering sheet 4 has transparency, adhesiveness to the tissue piece, flexibility, and some degree of strength. Materials having flexibility when they are formed into sheets can be preferably used as the material forming the covering sheet 4. Examples of the materials for the covering sheet 4 include polyolefin (for example, polyethylene, polypropylene, ethylene-propylene copolymer, ethylene-vinyl acetate copolymer), soft polyvinyl chloride (for example, polyvinyl chloride, vinyl chloride-vinyl acetate copolymer), polyester (for example, polyethylene terephthalate, polybutylene terephthalate), and polyamide. The thickness of the covering sheet 4 is set to favorably 0.5 to 3 mm and more favorably 0.7 to 2 mm.

Figure 8:
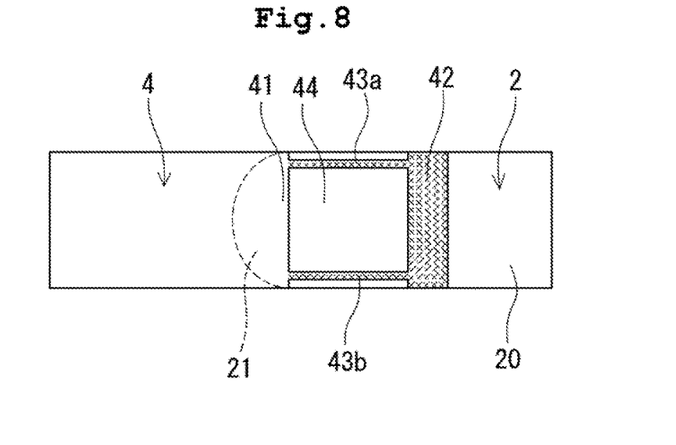
FIG. 8 is an explanatory view for explaining an internal construction of the tissue piece holder shown in FIG. 2.

As shown in FIGS. 7 and 8, the covering sheet 4 of this embodiment has the coverable part 40 extended at a predetermined length at its one end side, whereas the other end side part 42 of the covering sheet disposed at the other side of the covering sheet with respect to the fold-back portion 41 is sandwiched between the thermally conductive plate-shaped lower member 2 and the plate-shaped upper member 3. The other end side part (part to be sandwiched between the thermally conductive plate-shaped lower member and the plate-shaped upper member) 42 has an open portion 44. Thus, the other end side part (part to be sandwiched between the thermally conductive plate-shaped lower member and the plate-shaped upper member) has other end portion 42a and two connecting portions 43a, 43b extended to the one end side of the covering sheet 4 from the other end portion 42a.

The other end side part 42 (in other words, the other end side part disposed at the other side of covering sheet with respect to fold-back portion 41) is sandwiched between the thermally conductive plate-shaped lower member 2 and the plate-shaped upper member 3 and fixed thereto. The covering sheet 4 is foldable at the one end of the plate-shaped upper member 3, in other words, at the fold-back portion 41. The thermally conductive plate-shaped lower member 2 and the plate-shaped upper member 3 contact each other directly at the portion thereof where the covering sheet 4 is not sandwiched therebetween and fixed to each other. The covering sheet 4 of this embodiment has a concave portion at an outer side of each of the connecting portions 43a, 43b thereof.

As shown in FIG. 8, the covering sheet 4 is so disposed that its other end side part 42 is positioned on one end portion of the rectangular part of the thermally conductive plate-shaped lower member 2. Thereby the open portion 4 is positioned on the one end portion of the rectangular part of the thermally conductive plate-shaped lower member 2. As shown in FIGS. 3 through 6, the one end portion of the plate-shaped upper member 3 is fixedly disposed on the other end side part 42 of the covering sheet 4 in such a way that the cut-out part 32 of the plate-shaped upper member is located on the open portion 44 of the covering sheet 4. Therefore, in the tissue piece holder 1 of this embodiment, at the tissue piece placing part 5, the upper surface of the thermally conductive plate-shaped lower member 2 is exposed to the outside. Thus, the tissue piece placed at the tissue piece placing part 5 contacts the thermally conductive plate-shaped lower member 2, which allows the tissue piece to be satisfactorily cooled.

Figure 3:
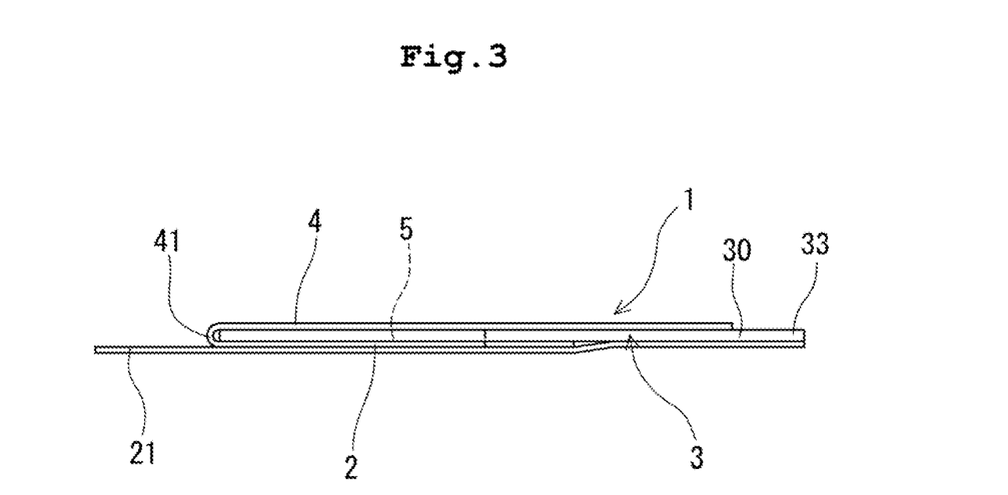
FIG. 3 is an enlarged bottom view of the tissue piece holder shown in FIG. 2.
Figure 4:
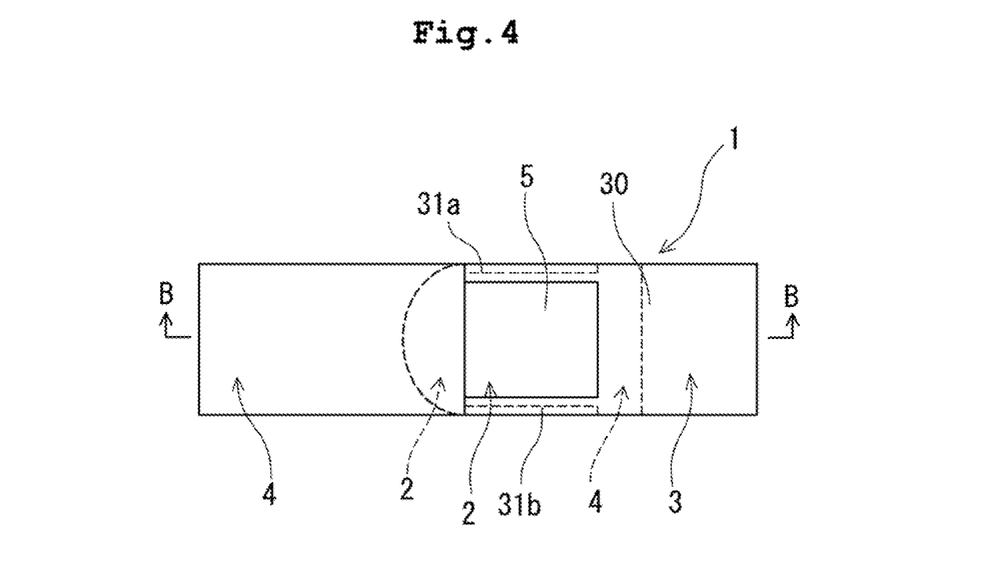
FIG. 4 is a front view of a state in which a covering sheet of the tissue piece holder shown in FIG. 2 is unfolded.
Figure 5:
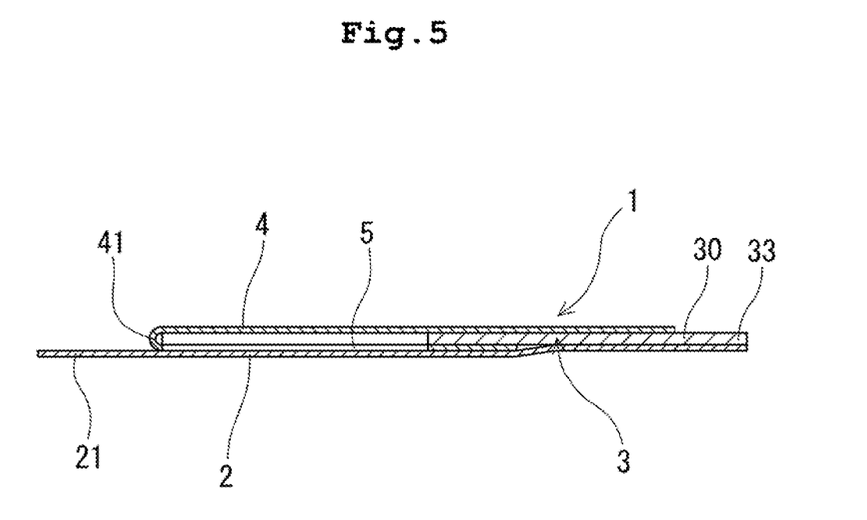
FIG. 5 is a sectional vie taken along a line A-A of FIG. 2.
Figure 6:
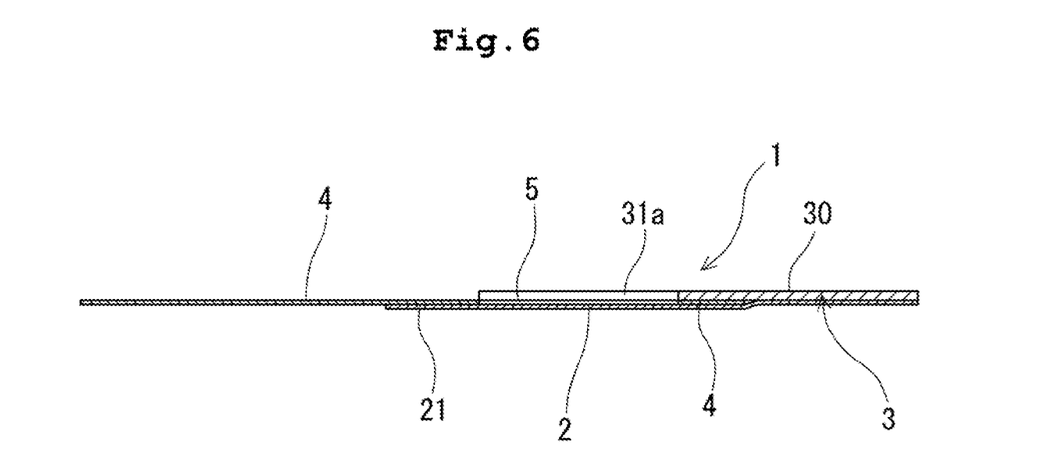
FIG. 6 is a sectional view taken along a line B-B of FIG. 4.

More specifically, the tissue piece placing part 5 is formed of the upper surface of a part, of the thermally conductive plate-shaped lower member 2, which is surrounded with the inner edge of the cut-out part of the plate-shaped upper member 3. As shown in FIGS. 3 and 5, the tissue piece placing part is formed as a concave portion having a depth equal to the total of the thickness of the plate-shaped upper member 3 and that of the covering sheet 4. Although the tissue piece placing part having the above-described construction is preferable, it is possible that the covering sheet 4 does not have the open portion and that the upper surface of the thermally conductive plate-shaped lower member 2 is covered with the covering sheet 4 at the tissue piece placing part 5.

By folding hack the covering sheet 4, the covering sheet is capable of entirely covering the tissue piece placing part 5 and the peripheral portion thereof and in addition the entirety or a part of the other end portion of the plate-shaped upper member 3. In this embodiment, as shown in FIG. 2, when the covering sheet 4 is folded back (in other words, when the tissue piece placing part is coved with the covering sheet), one end of the covering sheet does not reach the other end of the plate-shaped upper member 3. Therefore, when the tissue piece placing part is covered with the covering sheet, the other end portion 33 of the plate-shaped upper member 3 is exposed to the outside. This form allows the covering sheet 4 to be easily peeled off the plate-shaped upper member.

Figure 13:
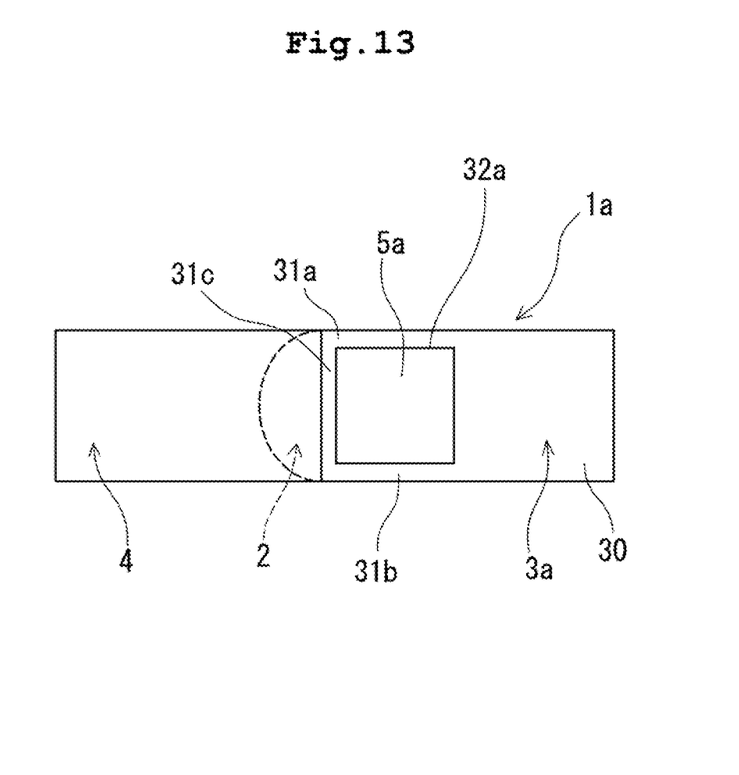
FIG. 13 is a front view of a state in which a covering sheet of a tissue piece holder for use in a collected living tissue cryopreserving tool of another embodiment of the present invention is unfolded.

Like a tissue piece holder 1a of an embodiment shown in FIG. 13, the tissue piece holder of the present invention may be so constructed that a plate-shaped upper member 3a has a cut-out part 32a and a tissue piece placing part 5a whose peripheral portions are surrounded with the plate-shaped upper member 3a. The entire periphery of the cut-out part 32a of this embodiment is surrounded with the flat plate part 30, the extended portions 31a, 31b, and an extended portion connecting portion 31c. Thus, the entire tissue piece placing part 5a is formed as a concave part. The construction of the extended portions 31a, 31b is similar to that of the above-described tissue piece holder 1. It is preferable to set the width of the extended portion connecting portion 31c equally to or smaller than that of the extended portions 31a, 31b.

Figure 15:
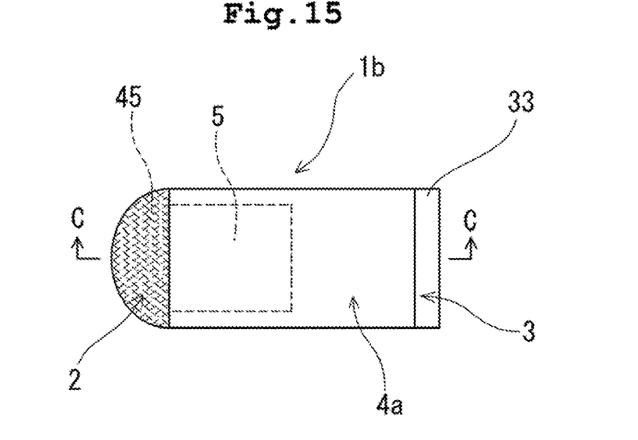
FIG. 15 is a front view of a tissue piece holder for use in a collected living cryopreserving tool of still another embodiment of the present invention.
Figure 16:
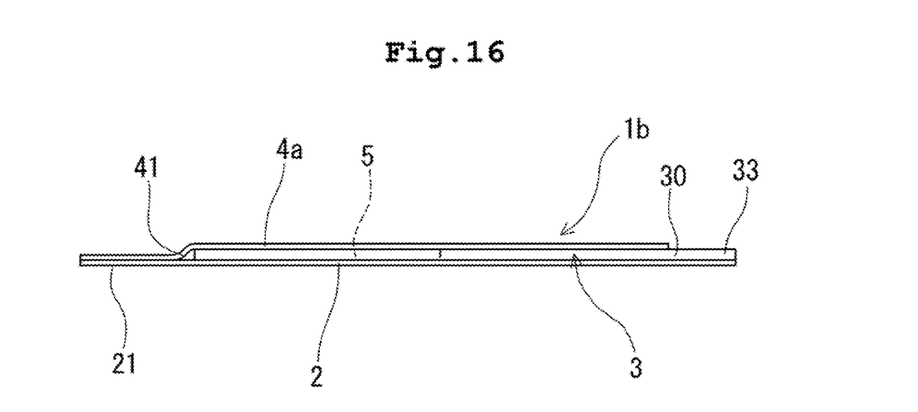
FIG. 16 is an enlarged bottom view of the tissue piece holder shown in FIG. 15.
Figure 17:
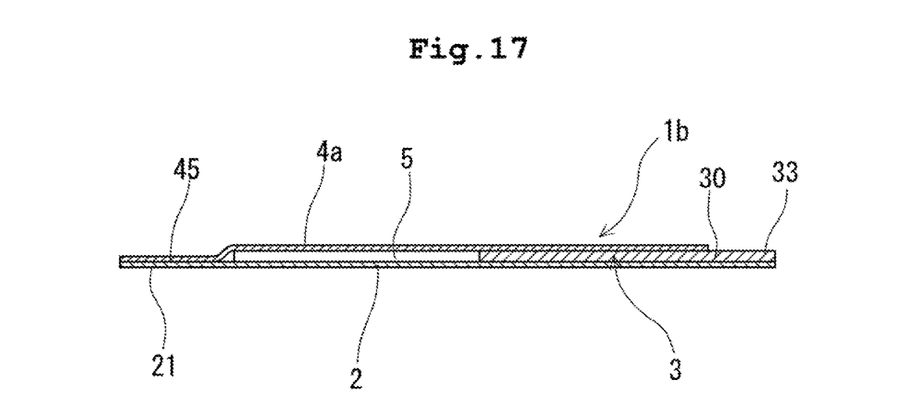
FIG. 17 is a sectional view taken along a line C-C of FIG. 15.

The tissue piece holder of the present invention may be formed like a tissue piece holder 1b of an embodiment shown in FIGS. 15 through 17.

As with the tissue piece holder of the above-described embodiment, the tissue piece holder 1b used in the collected living tissue cryopreserving tool of this embodiment cab be accommodated inside the resin-made accommodating bag 11 and is composed of the thermally conductive plate-shaped body part and the covering sheet 4a held by the plate-shaped body part. The tissue piece holder 1b has the tissue piece placing part 5 provided on the plate-shaped body part. The covering sheet 4a is capable of entirely covering the tissue piece placing part 5 and the peripheral portion of the tissue piece placing part.

As shown in FIGS. 15 through 17, the tissue piece holder 1b is composed of the plate-shaped body part and the covering sheet 4a held by the plate-shaped body part. The plate-shaped body part is composed of the thermally conductive plate-shaped lower member 2 and the plate-shaped upper member 3 fixed to the upper surface of the thermally conductive plate-shaped lower member 2. The thermally conductive plate-shaped lower member 2 and the plate-shaped upper member 3 are the same as those of the above-described tissue piece holder 1. The thermally conductive plate-shaped lower member 2 and the plate-shaped upper member 3 may be formed integrally with each other.

The plate-shaped upper member 3 has the cut-out part 32 extended from its one end side toward its other end side. The plate-shaped upper member 3 of this embodiment is so disposed that the one end thereof having the cut-out part 32 is positioned in the vicinity of the one end of the approximately rectangular part of the thermally conductive plate-shaped lower member 2. In this embodiment, the cut-out part 32 is extended at a predetermined length from the one end (in the vicinity of one end of rectangular part 20 of thermally conductive plate-shaped lower member 2) of the plate-shaped upper member 3 toward its other end side. Therefore, as shown in FIG. 7, the plate-shaped upper member 3 has the two extended portions 31a, 31b projected from the one end of the flat plate part 30.

As with the above-described tissue piece holder, the tissue piece holder 1b has the tissue piece placing part 5 formed on the upper surface of the plate-shaped body part. As with the above-described tissue piece holder 1, the tissue piece placing part 5 is formed of the cut-out part 32 provided on the plate-shaped upper member 3 and a part, of the upper surface of the thermally conductive plate-shaped lower member 2, which is disposed at the cut-out part 32. The size of the tissue piece placing part 5 is as described previously.

As shown in FIG. 15, the covering sheet 4a is capable of entirely covering the tissue piece placing part 5 and the peripheral portion of the tissue piece placing part 5. In the covering sheet 4a of this embodiment, as shown in FIGS. 15 and 17, one end side part of the covering sheet 4a is formed as the coverable part 40 capable of covering the tissue piece placing part 5, whereas the other end side part 45 thereof is fixed to the upper surface of the one end portion of the plate-shaped body part. More specifically, the other end side part of the covering sheet is fixed to the upper surface of the one end portion of the thermally conductive plate-shaped lower member 2. Therefore, normally, the covering sheet 4a entirely covers the tissue piece placing part 5 and the peripheral portion of the tissue piece placing part 5. By folding back the covering sheet 4a, it is possible to expose the entire tissue piece placing part 5 and the peripheral portion of the tissue piece placing part 5 to the outside.

The covering sheet 4a of this embodiment is extended beyond the tissue piece placing part 5 and capable of covering a part of an upper surface of the plate-shaped upper member between one end of the plate-shaped upper member and the tissue piece placing part 5 or almost an entirety of the upper surfaces of the plate-shaped upper member between one end of the plate-shaped upper member and the tissue piece placing part 5. As in the case of the above-described tissue piece holder, in the tissue piece holder 1b of this embodiment, as shown in FIG. 15, when the plate-shaped upper member 3 is covered with the covering sheet 4a, the other end portion 33 of the plate-shaped upper member 3 is exposed to the outside. The above-described covering sheet can be preferably used as the covering sheet 4a.

The resin-made accommodating bag 11 for accommodating the tissue piece holder 1 is described below.

The resin-made transparent accommodating bag 11 has a form capable of accommodating the tissue piece holder 1 therein. The peripheral portion of the resin-made transparent accommodating bag 11 is partly open to allow the tissue piece holder to be inserted thereinto.

More specifically, the resin-made transparent accommodating bag 11 is formed by laminating two rectangular transparent resin films on each other and heat-sealing three sides 16 of both films to each other. An open portion is formed of sides of both films not heat-sealed. The open portion can be heat-sealed with the resin-made transparent accommodating bag 11 accommodating the tissue piece holder 1 therein. The open portion of the resin-made transparent accommodating bag 11 forms a sealing portion 17 as shown in FIG. 12.

Figure 14:
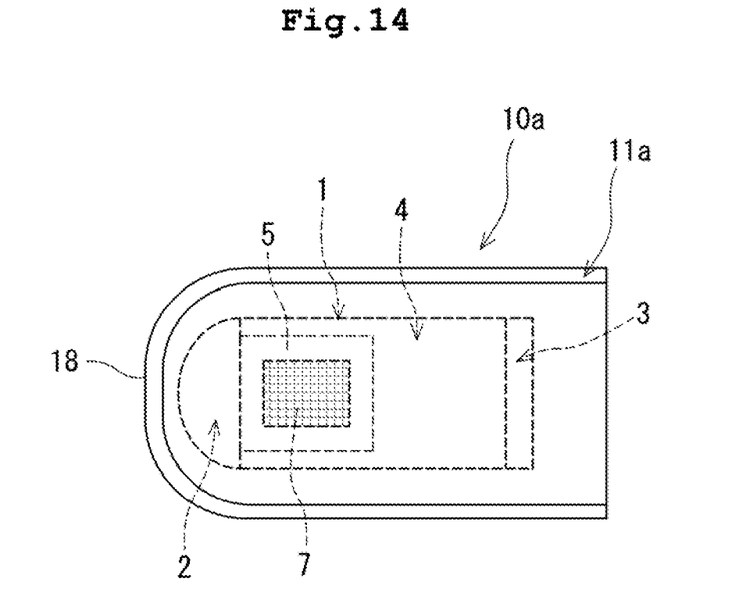
FIG. 14 is a front view of still another embodiment of a collected living tissue cryopreserving tool of the present invention.

Like a resin-made transparent accommodating bag 11a for use in a collected living tissue cryopreserving tool 10a of an embodiment shown in FIG. 14, the resin-made transparent accommodating bag may have a one end portion 18 rounded at both corners thereof. In the resin-made transparent accommodating bag of this embodiment, both corners of the one end portion as well as the one end portion and the heat-sealed portion at the one end portion are rounded. In a case where the tissue piece holder 1 rounded at its one end portion is used, it is advisable to insert the tissue piece holder into the resin made transparent accommodating bag having the above-described form from the rounded one end portion thereof. Thereby the degree of the peeling of the covering sheet is low in inserting the tissue piece holder 1 into the resin-made transparent accommodating bag 11a. In addition, it is possible to decrease the degree of the movement of the tissue piece holder 1 accommodated inside the resin-made transparent accommodating bag 11a.

Figure 11:
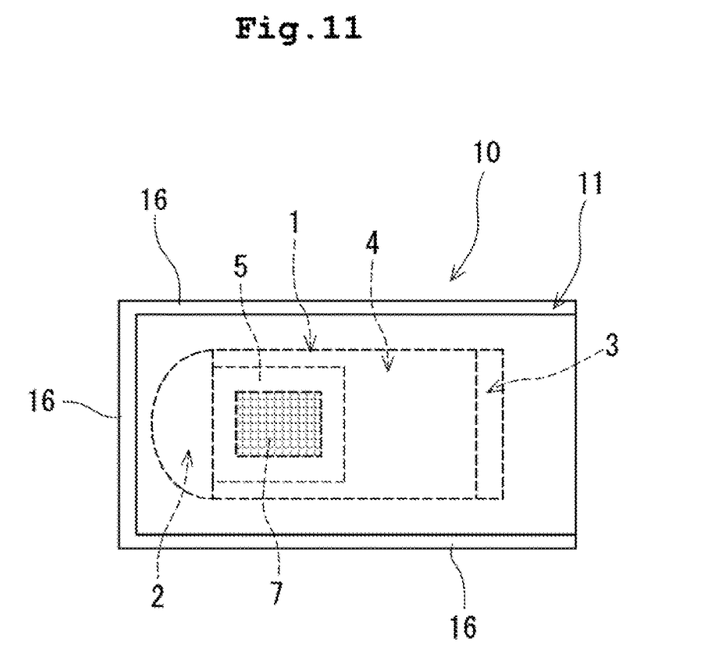
FIG. 11 is an explanatory view for explaining the action of the collected living tissue cryopreserving tool of the present invention.
Figure 12:
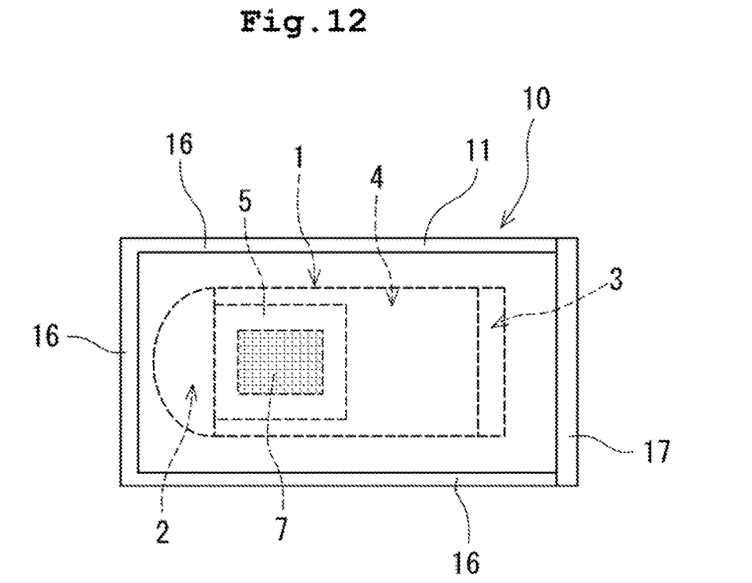
FIG. 12 is an explanatory view for explaining the action of the collected living tissue cryopreserving tool of the present invention.

The resin-made accommodating 11 is made of resin resistant to liquid nitrogen and is transparent as shown in FIGS. 1, 11, and 12. It is preferable to form the resin-made accommodating bag 11 by laminating two resin films each having an outer layer (for example, high-density polyethylene, polyethylene terephthalate) resistant to the liquid nitrogen and a hear-sealable inner layer (low melting point polyethylene) on each other with the heat-sealable inner layers being opposed to each other and by heat-sealing peripheral edges of the inner layers to each other in the shape of U. It is preferable to form the outer layer of a biaxially oriented film. For example, it is preferable to use a biaxially oriented polyester film (biaxially oriented polyethylene terephthalate film) a biaxially oriented polypropylene film, a biaxially oriented polystyrene film, a biaxially oriented polyamide film, and a high-density biaxially oriented polyethylene film. It is especially preferable that these films are transparent.

The collected living tissue cryopreserving tool of the present invention is particularly effective as an ovarian tissue piece cryopreserving tool. In addition, the collected living tissue cryopreserving tool can be effectively utilized as a liver tissue piece cryopreserving tool.

The collected tissue piece freezing method (method for freezing collected tissue piece by vitrification) to be carried out by using the collected living tissue cryopreserving tool 10 is described below with reference to FIGS. 9 through 12.

The collated tissue piece freezing method of the present invention is carried out by using the above-described collected living tissue cryopreserving tool. The collected tissue piece freezing method includes a tissue piece immersing step of immersing a collected tissue piece in a vitrification solution; a tissue piece placing step of placing the tissue piece taken out from the vitrification solution on the tissue piece placing part of the tissue piece holder; a tissue piece covering step of covering the tissue piece placed on the tissue piece placing part with the covering sheet and bringing the covering sheet into close contact with the tissue piece; an accommodating and sealing step of accommodating the tissue piece holder holding the tissue piece inside the accommodating bag without bringing the tissue piece holder into contact with a cooling medium and heat-sealing the open portion of the accommodating bag; and a freezing step of freezing the tissue piece by accommodating the tissue piece holder inside the accommodating bag, and bringing the sealed collected living tissue cryopreserving tool into contact with the cooling medium.

In the collected tissue piece freezing method of the present invention, initially, a tissue piece collecting step of collecting a tissue piece 7 from a living tissue to be cryopreserved is performed.

The tissue piece can be collected from the living tissue to be cryopreserved (for example, living organ such as ovary taken out from living body) by using a tissue cutting position-specifying tool as disclosed in Japanese Patent Application Laid-Open Publication No. 2008-222640. The tissue piece 7 may be collected by using a normal scalpel or the like. The tissue piece 7 is collected such that the size thereof is placeable on a surface of the tissue piece placing part 5 of the tissue piece holder 1.

Thereafter the tissue piece solution immersing step of immersing the collected tissue piece 7 in the vitrification solution is performed.

The tissue piece vitrification solution immersing step is performed by immersing the collected tissue piece in the vitrification solution. It is possible to use vitrification solutions conventionally used. More specifically, it is preferable to use the vitrification solutions containing one kind or not less than two kinds of a membrane-permeable cryoprotectant selected from among glycerol, propylene glycol, dimethylsulfoxide (DMSO), ethylene glycol, and butanediol and one kind or not less than two kinds of a membrane-impermeable cryoprotectant selected from among sucrose, trehalose, percoll, polyethylene glycol, polyvinyl pyrrolidone, bovine serum albumin, and ficoll.

It is preferable to perform treatment of immersing the collected tissue piece in an equilibrium liquid before the collected tissue piece is immersed in the vitrification solution. As the equilibrium liquid, a low-concentration solution of the membrane-permeable cryoprotectant is preferable. As the membrane-permeable cryoprotectant, it is possible to use the above-described substances.

After the execution of the step of immersing the tissue piece in the vitrification solution finishes, the tissue piece placing step of placing the tissue piece taken out from the vitrification solution on the tissue piece placing part 5 of the tissue piece holder 1 is performed.

Figure 9:
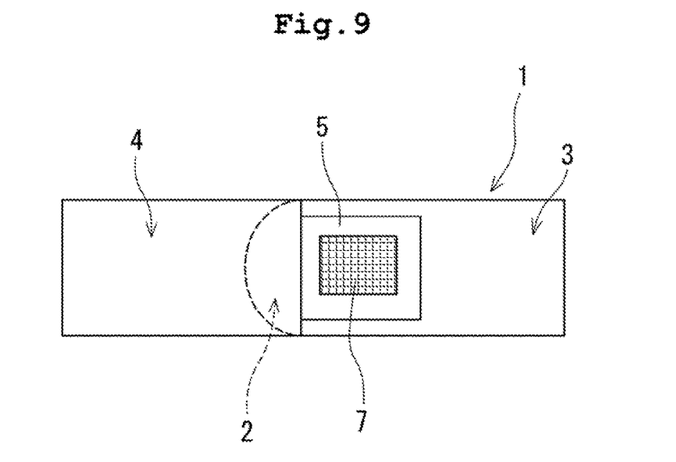
FIG. 9 is an explanatory view for explaining the action of the collected living tissue cryopreserving tool of the present invention.

At this step, as shown in FIG. 9, after the covering sheet 4 of the tissue piece holder 1 is unfolded to place the tissue piece placing part 5 into an exposed state, the tissue piece 7 taken out from the vitrification solution is placed on the tissue piece placing part 5 without bringing the tissue piece into contact with the cooling medium. In the operation of placing the tissue piece on the tissue piece placing part 5, the tissue piece is not cryopreserved by vitrification.

Figure 10:
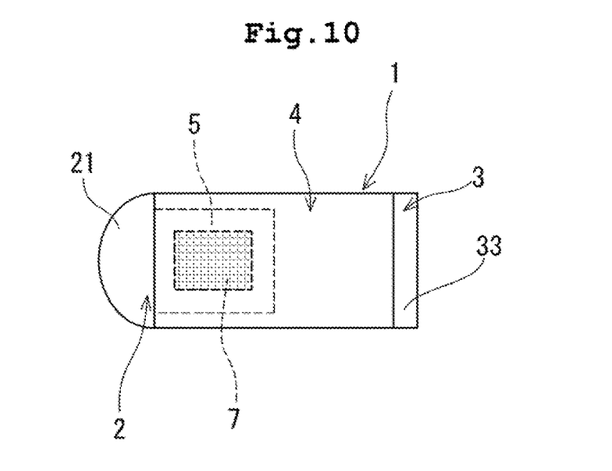
FIG. 10 is an explanatory view for explaining the action of the collected living tissue cryopreserving tool of the present invention.

Thereafter as shown in FIG. 10, the tissue piece covering step of covering the tissue piece 7 placed on the tissue piece placing part 5 with the coveting sheet 4 and bringing the covering sheet 4 into close contact with the tissue piece is performed. This step can be performed by folding back the covering sheet 4 and bringing the inner surface of the coverable part 40 of the folded back covering sheet 4 into close contact with the tissue piece 7. By carrying out this step, the upper surface of the tissue piece 7 is covered with the covering sheet, with the tissue piece being entirely capsulated by the tissue piece holder 1. In this state, the tissue piece holder 1 holds the tissue piece 7.

Subsequently the accommodating bag sealing step of accommodating the tissue piece holler 1 holding the collected tissue piece inside the resin-made accommodating bag 11 and heat-sealing the open portion thereof is carried out.

At this step, as shown in FIG. 11, the tissue piece holder 1 holding the tissue piece 7 is accommodated inside the resin-made accommodating bag 11 by inserting the tissue piece holder into the resin-made accommodating bag from its one end side rounded at both corners thereof. Thereafter as shown in FIG. 12, by sealing the open portion of the resin-made accommodating bag 11 with a heat sealer, the open portion is formed as the sealed portion 17. Thereby the tissue piece holder 1 is enclosed inside the resin-made accommodating bag 11. In this manner, the sealed collected living tissue cryopreserving tool 10 is prepared.

Thereafter the freezing step of freezing the tissue piece is performed by bringing the sealed collected living tissue cryopreserving tool 10 into contact with the cooling medium.

This step is performed by supplying the sealed collected living tissue cryopreserving tool 10 to a container filled with the cooling medium (generally, liquid nitrogen). Caused by the contact between the collected living tissue cryopreserving tool and the cooling medium, the resin-made accommodating bag 11, the tissue piece holder 1, and the tissue piece 7 are cooled. Because the tissue piece 7 contains the vitrification solution (more specifically, intracellular fluid is replaced with vitrification solution to some extent), the tissue piece is not crystallized but vitrified when the tissue piece is frozen. The tissue piece is preserved in this state until it is used.

INDUSTRIAL APPLICABILITY

The collected living tissue cryopreserving tool of the present invention has the following form.

(1) A collected living tissue cryopreserving tool for cryopreserving a collected living tissue piece in a sealed state, said collected living tissue cryopreserving tool comprising a tissue piece holder capable, of holding said living tissue piece and a resin-made accommodating bag which is capable of accommodating said tissue piece holder therein, sealable by being heat-sealed after accommodating said tissue piece holder therein, and resistant to liquid nitrogen, wherein said tissue piece holder comprises a plate-shaped body part composed of a thermally conductive plate-shaped lower member and a plate-shaped upper member fixed to an upper surface of said thermally conductive plate-shaped lower member and a covering sheet held by said plate-shaped body part; said tissue piece holder has a tissue piece placing part formed of a cut-out part provided on said plate-shaped upper member and a part, of said upper surface of said thermally conductive plate-shaped lower member, which is disposed at said cut-out part; and said covering sheet is capable of entirely covering said tissue piece placing part and a peripheral portion of said tissue piece placing part.

By placing the collected living tissue piece treated for vitrification on the tissue piece placing part of the tissue piece holder and covering the living tissue piece with the covering sheet, the tissue piece is held by the tissue piece holder and is not exposed to the outside. Further, by accommodating the tissue piece holder holding the tissue piece inside the resin-made accommodating bag and sealing the open portion thereof, the tissue piece holder itself can be sealed. Thereafter by bringing the tissue piece holder sealed inside the accommodating bag into contact with the cooling medium, the tissue piece is satisfactorily cooled. In this manner, the sealed living tissue piece can be rapidly frozen. Because in the collected living tissue cryopreserving tool, the tissue piece holder can be sealed by means of the accommodating bag during the cryopreservation of the tissue piece, the cooling medium does not enter the accommodating bag. Thus, the tissue piece holder does not contact the cooling medium. Therefore, it hardly occurs that the tissue piece holder deteriorates owing to the contact between the tissue piece holder and the cooling medium. Because the tissue piece holder does not contact the cooling medium, the collected tissue piece does not contact the cooling medium either. Furthermore, the liquid nitrogen is not substantially present inside the accommodating bag. Thus, when the accommodating bag is opened and when the covering sheet is peeled off the plate-shaped body part after the tissue piece is cryopreserved therein, it does not occur that the collected tissue piece scatters owing to the vaporization of the cooling medium.

The embodiment of the present invention may be as described below.

(2) A collected living tissue cryopreserving tool according to the above (1), wherein said covering sheet has transparency and adhesiveness to said tissue piece.

(3) A collected living tissue cryopreserving tool according to the above (1) or (2), wherein one end side part of said covering sheet is formed as a coverable part capable of cover said tissue piece placing part and said peripheral portion of said tissue piece placing part; other end side part of said covering sheet is sandwiched between said thermally conductive plate-shaped lower member and said plate-shaped upper member; and said covering sheet is foldable at one end of said plate-shaped upper member.

(4) A collected living tissue cryopreserving tool according to any one of the above (1) through (3), wherein said covering sheet is extended beyond said tissue piece placing part and capable of covering a part of an upper surface of said plate-shaped upper member between one end of said plate-shaped upper member and said tissue piece placing part or almost an entirety of said upper surfaces of said plate-shaped upper member between one end of said plate-shaped upper member and said tissue piece placing part.

(5) A collected living tissue cryopreserving tool according to any one of the above (1) through (4), wherein said thermally conductive plate-shaped lower member has a one end portion rounded in both corners thereof and an approximately rectangular part extended from said one end portion to the other end portion thereof.

(6) A collected living tissue cryopreserving tool according to any one of the above (1) through (5), wherein said plate-shaped upper member has said cut-out part extended from one end side thereof toward the other end side thereof.

(7) A collected living tissue cryopreserving tool according to the above (6), wherein said plate-shaped upper member is so disposed that said one, end thereof having said cut-out part is positioned in a vicinity of one end of said approximately rectangular part of said thermally conductive plate-shaped lower member.

(8) A collected living tissue cryopreserving tool according to any one of the above (1) through (7), wherein at said tissue piece placing part, said upper surface of said thermally conductive plate-shaped lower member is exposed to the outside.

(9) A collected living tissue cryopreserving tool according to any one of the above (1) through (8), wherein when said plate-shaped upper member is covered with said covering sheet, the other end portion of said plate-shaped upper member is exposed to the outside.

Also, the collected living tissue cryopreserving tool of the present invention has the following form.

(10) A collected living tissue cryopreserving tool for cryopreserving a collected living tissue piece in a sealed state, said collected living tissue cryopreserving tool comprising a tissue piece holder capable of holding said living tissue piece and a resin-made accommodating bag which is capable of accommodating said tissue piece holder therein, sealable by being heat-sealed after accommodating said tissue piece holder therein, and resistant to liquid nitrogen, wherein said tissue piece holder comprises a thermally conductive plate-shaped body part and a covering sheet held by said plate-shaped body pare said tissue piece holder has a tissue piece placing part formed on said plate-shaped body part; and said covering sheet is capable of entirely covering said tissue piece placing part and a peripheral portion of said tissue piece placing part.

By placing the collected living tissue piece treated for vitrification on the tissue piece placing part of the tissue piece holder and covering the living tissue piece with the covering sheet, the tissue piece is held by the tissue piece holder and is not exposed to the outside. Further, by accommodating the tissue piece holder holding the tissue piece inside the resin-made accommodating bag and sealing the open portion thereof, the tissue piece holder itself can be sealed. Thereafter by bringing the tissue piece holder sealed inside the accommodating bag into contact with the cooling medium, the tissue piece is satisfactorily cooled. In this manner, the sealed living tissue piece can be rapidly frozen. Because in the collected living tissue cryopreserving tool, the tissue piece holder can be sealed by means of the accommodating bag during the cryopreservation of the tissue piece, the cooling medium does not enter the accommodating bag. Thus, the tissue piece holder does not contact the cooling medium. Therefore, it hardly occurs that the tissue piece holder deteriorates owing to the contact between the tissue piece holder and the cooling medium. Because the tissue piece holder does not contact the cooling medium, the collected tissue piece does not contact the cooling medium either. Furthermore, the liquid nitrogen is not substantially present inside the accommodating bag. Thus, when the accommodating bag is opened and when the covering sheet is peeled off the plate-shaped body part after the tissue piece is cryopreserved therein, it does not occur that the collected tissue piece scatters owing to the vaporization of the cooling medium.

The embodiment of the present invention may be as described below.

(11) A collected living tissue cryopreserving tool according to any one of the above (1) through (10), wherein said resin-made accommodating bag has a resin-made outer layer resistant to liquid nitrogen and a heat-sealable inner layer.

(12) A collected living tissue cryopreserving tool according to any one of the above (1) through (11), which is an ovarian tissue piece cryopreserving tool or a liver tissue piece cryopreserving tool.

(13) A collected living tissue cryopreserving tool according to any one of the above (10) through (12), wherein said covering sheet has transparency and adhesiveness to said tissue piece.

The collected tissue piece freezing method of the present invention is as described below.

(14) A collected tissue piece freezing method to be carried out by using a collected living tissue cryopreserving tool according to any one of the above (1) through (13), said collected tissue piece freezing method comprising a tissue piece immersing step of immersing a collected tissue piece in a vitrification solution; a tissue piece placing step of placing said tissue piece taken out from said vitrification solution on said tissue piece placing part of said tissue piece holder; a tissue piece covering step of covering said tissue piece placed on said tissue piece placing part with said covering sheet and bringing said, covering sheet into close contact with said tissue piece; an accommodating and sealing step of accommodating said tissue piece holder holding said tissue piece inside said accommodating bag without bringing said tissue piece holder into contact with a cooling medium and heat-sealing an open portion of said accommodating bag; and a freezing step of freezing said tissue piece by accommodating said tissue piece holder inside said accommodating bag and bringing said sealed collected living tissue cryopreserving tool into contact with said cooling medium.

According to the collected tissue piece freezing method, the operation of freezing the collected living tissue piece can be easily and reliably performed.

The embodiment of the present invention may be as described below.

(15) A collected tissue piece freezing method according to the above (14), which is an ovarian tissue piece freezing method or a liver tissue piece freezing method.

The invention claimed is:

1. A tissue cryopreserving tool comprising:
   a holder, said holder comprising a plate-shaped body and a covering sheet held to said plate-shaped body; and
   a resin bag for accommodating said holder therein, wherein
   said plate-shaped body comprises a thermally conductive plate-shaped lower member and a plate-shaped upper member fixed to an upper surface of said thermally conductive plate-shaped lower member,
   said plate-shaped upper member has a cut-out part,
   said cut-out part of said plate-shaped upper member and said upper surface of said thermally conductive plate-shaped lower member defining a tissue piece placing part of the plate-shaped body,
   said covering sheet is configured to entirely cover said tissue piece placing part and a portion peripheral to said tissue piece placing part, and
   said resin bag has an open portion, to allow said holder to be inserted thereinto, and has resistance to liquid nitrogen, and said open portion of said resin bag is configured to be heat-sealable.

2. A tissue cryopreserving tool according to claim 1, wherein said covering sheet is transparent.

3. A tissue cryopreserving tool according to claim 1, wherein said covering sheet has a part sandwiched between said thermally conductive plate-shaped lower member and said plate-shaped upper member.

4. A tissue cryopreserving tool according to claim 1, wherein said covering sheet is extended beyond said tissue piece placing part and configured to cover at least a part of an upper surface of said plate-shaped upper member between one end of said plate-shaped upper member and said tissue piece placing part.

5. A tissue cryopreserving tool according to claim 1, wherein said thermally conductive plate-shaped lower member has a rectangular shape with a first end having rounded corners.

6. A tissue cryopreserving tool according to claim 1, wherein said plate-shaped upper member has said cut-out part extended from one end side thereof toward an other end side thereof.

7. A tissue cryopreserving tool according to claim 6, wherein said plate-shaped upper member is so disposed that said one end side thereof having said cut-out part is positioned in one end of a rectangular part of said thermally conductive plate-shaped lower member.

8. A tissue cryopreserving tool according to claim 1, wherein said resin bag has a liquid nitrogen resistant outer layer and an inner layer for heat sealing.

9. A tissue cryopreserving tool comprising:
   a holder having a plate-shaped body;
   a covering sheet; and
   a resin bag for accommodating said holder therein, wherein
   said resin bag has an open portion configured to allow said holder to be inserted thereinto and has resistance to liquid nitrogen, and said open portion of said resin bag is configured to be heat-sealable,
   said plate-shaped body of said holder is thermally conductive and has a concave part for placing a living tissue piece, and
   said covering sheet is configured to entirely cover said concave part and a peripheral portion of said plate-shaped body surrounding said concave part.

10. A tissue cryopreserving tool according to claim 9, wherein said covering sheet is transparent.

11. A collected tissue piece freezing method to be carried out by using a cryopreserving tool according to claim 9,
   said collected tissue piece freezing method comprising a tissue piece immersing step of immersing a collected tissue piece in a vitrification solution; a tissue piece placing step of placing said tissue piece taken out from said vitrification solution on said tissue piece placing part of said holder; a tissue piece covering step of covering said tissue piece placed on said tissue piece placing part with said covering sheet and bringing said covering sheet into contact with said tissue piece; an accommodating and sealing step of accommodating said holder holding said tissue piece inside said resin bag without bringing said holder into contact with a cooling medium and heat-sealing an open portion of said resin bag; and a freezing step of freezing said tissue piece by bringing said sealed tissue cryopreserving tool into contact with said cooling medium while said holder is accommodated inside said resin bag.

12. A collected tissue piece freezing method according to claim 11, wherein the tissue piece is an ovarian tissue piece or a liver tissue piece.

* * * * *